United States Patent
Bay-Jensen et al.

(10) Patent No.: US 11,531,028 B2
(45) Date of Patent: Dec. 20, 2022

(54) COLLAGEN TYPE X ALPHA-1 ASSAY

(71) Applicant: Nordic Bioscience A/S, Herlev (DK)

(72) Inventors: Anne Christine Bay-Jensen, Kobenhavn S (DK); Yi He, Ballerup (DK); Morten Karsdal, Kobenhavn Ø (DK)

(73) Assignee: Nordic Bioscience A/S, Herlev (DK)

(*) Notice: Subject to any disclaimer, the term of this patent is extended or adjusted under 35 U.S.C. 154(b) by 258 days.

(21) Appl. No.: 16/779,602

(22) Filed: Feb. 1, 2020

(65) Prior Publication Data

US 2020/0158726 A1 May 21, 2020

Related U.S. Application Data

(63) Continuation-in-part of application No. 14/889,905, filed as application No. PCT/EP2014/059584 on May 9, 2014, now abandoned.

(30) Foreign Application Priority Data

May 10, 2013 (GB) .................................. 1308396

(51) Int. Cl.
*G01N 33/564* (2006.01)
*G01N 33/68* (2006.01)
*C07K 16/18* (2006.01)

(52) U.S. Cl.
CPC .......... *G01N 33/564* (2013.01); *C07K 16/18* (2013.01); *G01N 33/6887* (2013.01); *C07K 2317/34* (2013.01); *G01N 2333/78* (2013.01)

(58) Field of Classification Search
None
See application file for complete search history.

(56) References Cited

U.S. PATENT DOCUMENTS 6,288,214 B1 9/2001 Hook et al.

FOREIGN PATENT DOCUMENTS

WO WO-2013126810 A1 * 8/2013 ............. A61K 39/00
WO WO-2014208760 A1 * 12/2014 ....... A61K 39/39558

OTHER PUBLICATIONS

Kwan et al., Abnormal Compartmentalization of Cartilage Matrix Components in Mice Lacking Collagen X: Implications for Function, The Journal of Cell Biology, vol. 136, No. 2, Jan. 27, 1997 459-471 (Year: 1997).*
Of Hancock et al. (2005) Synthetic Peptides as Antigens for Antibody Production. In: Burns R. (eds) Immunochemical Protocols. Methods In Molecular Biology™, vol. 295. Humana Press. https://doi.org/10.1385/1-59259-873-0:013 (Year: 2005).*

(Continued)

*Primary Examiner* — Rebecca M Giere
*Assistant Examiner* — Xiaoyan Zou
(74) *Attorney, Agent, or Firm* — Benjamin Aaron Adler

(57) ABSTRACT

An antibody specifically reactive with an epitope of collagen type X alpha 1 comprised in the NC1 domain C-terminal amino acid sequence SFSGFLVAPM-COOH (SEQ ID NO: 1), and a method of immunoassay for detecting in a biological sample an epitope in the NC1 domain C-terminal amino acid sequence SFSGFLVAPM-COOH (SEQ ID NO: 1) of collagen type X alpha 1, by contacting the biological sample with the antibody, and determining the amount of binding of the antibody.

8 Claims, 2 Drawing Sheets

Figure 1:
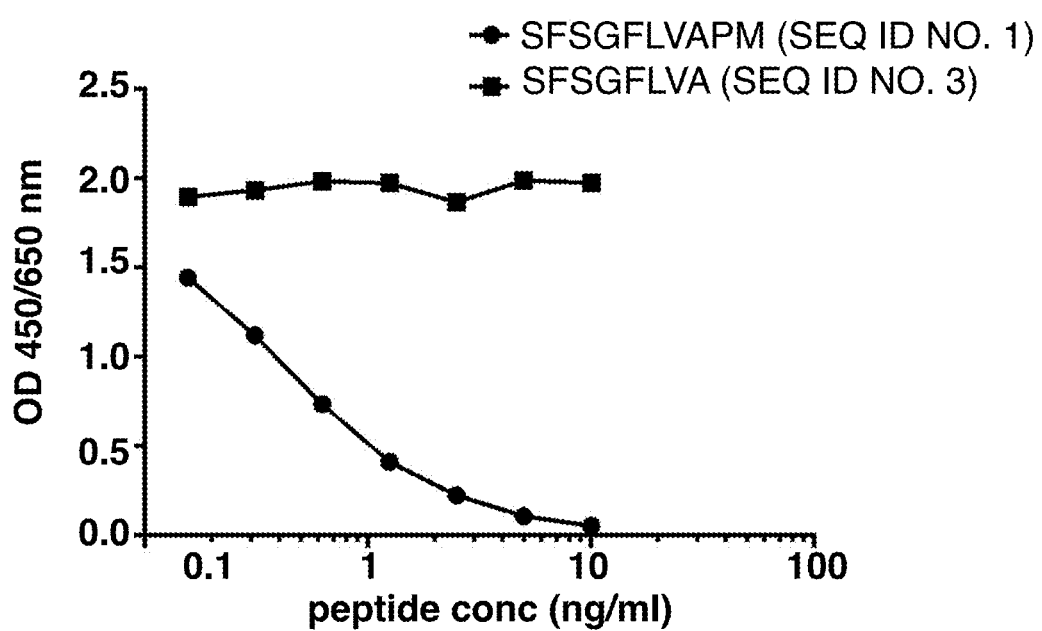

Specification includes a Sequence Listing.

(56) References Cited

OTHER PUBLICATIONS

Chan et al. A Nonsense Mutation in the Carboxyl-terminal Domain of Type X Collagen Causes Haploinsufficiency in Schmid Metaphyseal Chondrodysplasia, J. Clin. Invest. 101(7), 1998, 1490-1499 (Year: 1998).*
Girkontaite et al. Immunolocalization of Type X Collagen in Normal Fetal and Adult Osteoarthritic Cartilage with Monoclonal Antibodies, Matrix Biology 15, 231-238, 1996 (Year: 1996).*
Heras, the Biological Basis of Joint Ankylosis: studies in the ank/ank mouse; Thesis, http://hdl.handle.net/1807/26466, 2010 (Year: 2010).*
Xia et al. The constant region affects antigen binding of antibodies to DNA by altering secondary structure. Mol Immunol. Nov. 2013: 56(0): 28-37. doi:10.1016/j.molimm.2013.04.004 (Year: 2013).*
Torres et al. The immunoglobulin heavy chain constant region affects kinetic and thermodynamic parameters of antibody variable region interactions with antigen. J Biol Chem. May 4, 2007;282(18):13917-27. doi: 10.1074/jbc.M700661200. Epub Mar. 12, 2007. PMID: 17353196 (Year: 2007).*
Abhishek, A. and Doherty, M., Pathophysiology of articular chondrocalcinosis role of ANKH. Nat Rev Rheumatol, 7:96-104, 2011.
Kronenberg, H.M., Developmental regulation of the growth plate. Nature, 423:332-336, 2003.
Pfander, et al.. Expression of early and late differentiation markers (proliferating cell nuclear antigen, syndecan-3, annexin VI, and alkaline phosphatase) by human osteoarthritic chondrocytes Am J Pathol, 159:1777-83, 2001.
Von Der Mark, et al., Type X collagen synthesis in human osteoarthritic cartilage. Indication of chondrocyte hypertrophy. Arthritis Rheum, 35:806-11, 1992.
Fuerst, et al., Calcification of articular cartilage in human osteoarthritis. Arthritis Rheum, 60:2694-703, 2009.
Dreier, R., Hypertrophic differentiation of chondrocytes in osteoarthritis: the developmental aspect of degenerative joint disorders Arthritis Res Ther, 12:216, 2010.
Pitsillides, A.A. and Beier, F., Cartilage biology in osteoarthritis—lessons from developmental biology. Nat Rev Rheumatol, 7:654-63, 2011.
Van Der Kraan, P.M. and Van Den Berg, W.B., Chondrocyte hypertrophy and osteoarthritis: role in initiation and progression of cartilage degeneration? Osteoarthritis Cartilage, 20:223-232, 2012.
Frischolz, et al., J. Biol. Chem., 273:4547, 1998.
Yamaguchi, et al. J. Biol. Chem., 264:16022, 1989.
Gefter, et al. A simple method for polyethylene glycol-promoted hybridization of mouse myeloma cells. Somatic Cell Genet., 3:231-236, 1977.
Bay-Jensen, et al., Enzyme-linked immunosorbent assay (ELISAs) for metalloproteinase derived type II collagen neoepitope, CIIM-increased serum CIIM in subjects with severe radiographic osteoarthritis. Clin Biochem, 2011; 44:423-429, 2011.
Rucklidge, et al., Matrix Biol., 15:73, 1996.
Aigner, et al., Histochem. Cell Biol., 107:435, 1997.
Goldring, et al., Defining the roles of inflammatory and anabolic cytokines in cartilage metabolism. Ann Rheum Dis, 67:75-82, 2008.
Gerstenfeld, L.C. and Shapiro, F.D., Expression of bone-specific genes by hypertrophic chondrocytes: implication of the complex functions of the hypertrophic chondrocyte during endochondral bone development. J Cell Biochem, 62:1-9, 1996.
Wei, et al., Activation of Indian hedgehog promotes chondrocyte hypertrophy and upregulation of MMP-13 in human osteoarthritic cartilage Osteoarthritis Cartilage, 20:755-63, 2012.
Dong, et al., Wnt induction of chondrocyte hypertrophy through the Runx2 transcription factor. J Cell Physiol, 208:77-86, 2006.
Horner, et al., Immunolocalisation of vascular endothelial growth factor (VEGF) in human neonatal growth plate cartilage. J Anat, 194:519-24, 1999.
Tsuchiya, et al., Expression of mouse HtrA1 serine protease in normal bone and cartilage and its upregulation in joint cartilage damaged by experimental arthritis. Bone, 37:323-36, 2005.
Huebner, et al., Transglutaminase 2 is a marker of chondrocyte hypertrophy and osteoarthritis severity in the Hartley guinea pig model of knee OA. Osteoarthritis Cartilage, 17:1056-64, 2009.
Fitzgerald, et al., Shear- and compression-induced chondrocyte transcription requires MAPK activation in cartilage explants. J Biol Chem, 283:6735-43, 2008.
He, et al. Chondrocyte hypertrophy, measured by the secretion of collagen type X, is a hallmark of pathological changes in osteoarthritis, Osteoarthritis and Cartilage, 21(Supplement):S77, Apr. 1, 2013.

* cited by examiner

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial sequence
<220> FEATURE:
<223> OTHER INFORMATION: C-terminal epitope sequence in NC1 domain of
      collagen type VI alpha 1 as selection peptide

<400> SEQUENCE: 1

Ser Phe Ser Gly Phe Leu Val Ala Pro Met
1               5                   10

<210> SEQ ID NO 2
<211> LENGTH: 10
<212> TYPE: PRT
<213> ORGANISM: Artificial sequence
```

```
<220> FEATURE:
<223> OTHER INFORMATION: Modified C-terminal epitope sequence as a
      screening peptide
<220> FEATURE:
<221> NAME/KEY: SITE
<222> LOCATION: (1)
<223> OTHER INFORMATION: N-terminal Ser is biotinylated

<400> SEQUENCE: 2

Ser Phe Ser Gly Phe Leu Val Ala Pro Met
1               5                   10

<210> SEQ ID NO 3
<211> LENGTH: 8
<212> TYPE: PRT
<213> ORGANISM: Artificial sequence
<220> FEATURE:
<223> OTHER INFORMATION: Truncated peptide

<400> SEQUENCE: 3

Ser Phe Ser Gly Phe Leu Val Ala
1               5

<210> SEQ ID NO 4
<211> LENGTH: 13
<212> TYPE: PRT
<213> ORGANISM: Artificial sequence
<220> FEATURE:
<223> OTHER INFORMATION: Modified C-terminal epitope sequence as an
      immunogenic peptide
<220> FEATURE:
<221> NAME/KEY: SITE
<222> LOCATION: (1)..(3)
<223> OTHER INFORMATION: N-terminal Cys Gly Gly is a linker
<220> FEATURE:
<221> NAME/KEY: SITE
<222> LOCATION: (1)
<223> OTHER INFORMATION: N-terminal Cys is linked to Keyhole Limpet
      Hemocyanin

<400> SEQUENCE: 4

Cys Gly Gly Ser Phe Ser Gly Phe Leu Val Ala Pro Met
1               5                   10

<210> SEQ ID NO 5
<211> LENGTH: 11
<212> TYPE: PRT
<213> ORGANISM: Artificial sequence
<220> FEATURE:
<223> OTHER INFORMATION: Deselection peptide

<400> SEQUENCE: 5

Asp Met Asp Tyr Leu Pro Arg Val Pro Asn Gln
1               5                   10

<210> SEQ ID NO 6
<211> LENGTH: 16
<212> TYPE: PRT
<213> ORGANISM: Artificial sequence
<220> FEATURE:
<223> OTHER INFORMATION: Light chain complementary determining region
      CDR-L1 sequence

<400> SEQUENCE: 6

Arg Ser Ser Gln Ser Leu Val His Ser Asn Gly Tyr Thr Tyr Ser Asn
1               5                   10                  15
```

```
<210> SEQ ID NO 7
<211> LENGTH: 7
<212> TYPE: PRT
<213> ORGANISM: Artificial sequence
<220> FEATURE:
<223> OTHER INFORMATION: Light chain complementary determining region
      CDR-L2 sequence

<400> SEQUENCE: 7

Arg Val Ser Asn Arg Phe Ser
1               5

<210> SEQ ID NO 8
<211> LENGTH: 9
<212> TYPE: PRT
<213> ORGANISM: Artificial sequence
<220> FEATURE:
<223> OTHER INFORMATION: Light chain complementary determining region
      CDR-L3 sequence

<400> SEQUENCE: 8

Ser Gln Ser Thr His Val Pro Trp Thr
1               5

<210> SEQ ID NO 9
<211> LENGTH: 5
<212> TYPE: PRT
<213> ORGANISM: Artificial sequence
<220> FEATURE:
<223> OTHER INFORMATION: Heavy chain complementary determining region
      CDR-H1 sequence

<400> SEQUENCE: 9

Asp Thr His Met His
1               5

<210> SEQ ID NO 10
<211> LENGTH: 17
<212> TYPE: PRT
<213> ORGANISM: Artificial sequence
<220> FEATURE:
<223> OTHER INFORMATION: Heavy chain complementary determining region
      CDR-H2 sequence

<400> SEQUENCE: 10

Arg Ile Asp Pro Ala Asn Val Asn Thr Lys Tyr Asp Pro Arg Phe Gln
1               5                   10                  15

Gly

<210> SEQ ID NO 11
<211> LENGTH: 5
<212> TYPE: PRT
<213> ORGANISM: Artificial sequence
<220> FEATURE:
<223> OTHER INFORMATION: Heavy chain complementary determining region
      CDR-H3 sequence,

<400> SEQUENCE: 11

Ser Gly Ser Ser Pro
1               5

<210> SEQ ID NO 12
<211> LENGTH: 79
<212> TYPE: PRT
<213> ORGANISM: Artificial sequence
<220> FEATURE:
<223> OTHER INFORMATION: Light chain complementary determining regions
      and framework sequence
```

```
<400> SEQUENCE: 12

Arg Ser Ser Gln Ser Leu Val His Ser Asn Gly Tyr Thr Tyr Ser Asn
1               5                   10                  15

Trp Tyr Leu Gln Lys Pro Gly Gln Ser Pro Lys Leu Leu Ile Tyr Arg
                20                  25                  30

Val Ser Asn Arg Phe Ser Gly Val Pro Asp Arg Phe Ser Gly Ser Gly
            35                  40                  45

Ser Gly Thr Asp Phe Thr Leu Lys Ile Ser Arg Val Glu Ala Asp Asp
        50                  55                  60

Leu Gly Val Tyr Phe Cys Ser Gln Ser Thr His Val Pro Trp Thr
65                  70                  75

<210> SEQ ID NO 13
<211> LENGTH: 84
<212> TYPE: PRT
<213> ORGANISM: Artificial sequence
<220> FEATURE:
<223> OTHER INFORMATION: Heavy chain complementary determining regions
      and framework sequence

<400> SEQUENCE: 13

Asp Thr His Met His Trp Val Lys Gln Arg Pro Glu Gln Gly Leu Glu
1               5                   10                  15

Trp Ile Gly Arg Ile Asp Pro Ala Asn Val Asn Thr Lys Tyr Asp Pro
                20                  25                  30

Arg Phe Gln Gly Arg Ala Thr Ile Thr Ala Asp Thr Ser Ser Asn Thr
            35                  40                  45

Ala Tyr Leu Gln Leu Ser Arg Leu Thr Ser Glu Asp Thr Ala Val Tyr
        50                  55                  60

Tyr Cys Ala Thr Ser Gly Ser Ser Pro Trp Gly Gln Gly Thr Thr Leu
65                  70                  75                  80

Thr Val Ser Ser

<210> SEQ ID NO 14
<211> LENGTH: 112
<212> TYPE: PRT
<213> ORGANISM: Artificial sequence
<220> FEATURE:
<223> OTHER INFORMATION: Light chain variable region sequence

<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Tyr Thr Tyr Ser Asn Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110
```

-continued

```
<210> SEQ ID NO 15
<211> LENGTH: 114
<212> TYPE: PRT
<213> ORGANISM: Artificial sequence
<220> FEATURE:
<223> OTHER INFORMATION: Heavy chain variable region sequence

<400> SEQUENCE: 15
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

His Met His Trp Val Lys Gln Arg Pro Glu Gln Gly Leu Glu Trp Ile
        35                  40                  45

Gly Arg Ile Asp Pro Ala Asn Val Asn Thr Lys Tyr Asp Pro Arg Phe
    50                  55                  60

Gln Gly Arg Ala Thr Ile Thr Ala Asp Thr Ser Ser Asn Thr Ala Tyr
65                  70                  75                  80

Leu Gln Leu Ser Arg Leu Thr Ser Glu Asp Thr Ala Val Tyr Tyr Cys
                85                  90                  95

Ala Thr Ser Gly Ser Ser Pro Trp Gly Gln Gly Thr Thr Leu Thr Val
            100                 105                 110

Ser Ser

```
<210> SEQ ID NO 16
<211> LENGTH: 438
<212> TYPE: PRT
<213> ORGANISM: Artificial sequence
<220> FEATURE:
<223> OTHER INFORMATION: Heavy chain sequence of monoclonal antibody
      NB09-11G8, mouse IgG1 isotype

<400> SEQUENCE: 16
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

His Met His Trp Val Lys Gln Arg Pro Glu Gln Gly Leu Glu Trp Ile
        35                  40                  45

Gly Arg Ile Asp Pro Ala Asn Val Asn Thr Lys Tyr Asp Pro Arg Phe
    50                  55                  60

Gln Gly Arg Ala Thr Ile Thr Ala Asp Thr Ser Ser Asn Thr Ala Tyr
65                  70                  75                  80

Leu Gln Leu Ser Arg Leu Thr Ser Glu Asp Thr Ala Val Tyr Tyr Cys
                85                  90                  95

Ala Thr Ser Gly Ser Ser Pro Trp Gly Gln Gly Thr Thr Leu Thr Val
            100                 105                 110

Ser Ser Ala Lys Thr Thr Pro Pro Ser Val Tyr Pro Leu Ala Pro Gly
            115                 120                 125

Ser Ala Ala Gln Thr Asn Ser Met Val Thr Leu Gly Cys Leu Val Lys
        130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

```
Thr Val Thr Cys Asn Val Ala His Pro Ala Ser Ser Thr Lys Val Asp
            195                 200                 205

Lys Lys Ile Val Pro Arg Asp Cys Gly Cys Lys Pro Cys Ile Cys Thr
210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
        355                 360                 365

Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
            435

<210> SEQ ID NO 17
<211> LENGTH: 219
<212> TYPE: PRT
<213> ORGANISM: Artificial sequence
<220> FEATURE:
<223> OTHER INFORMATION: Light chain sequence of monoclonal antibody
      NB09-11G8, mouse Kappa isotype

<400> SEQUENCE: 17

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Tyr Thr Tyr Ser Asn Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

```
                                -continued

Arg Ala Asp Ala Ala Pro Thr Val Ser Ile Phe Pro Pro Ser Ser Glu
        115             120             125

Gln Leu Thr Ser Gly Gly Ala Ser Val Val Cys Phe Leu Asn Asn Phe
    130             135             140

Tyr Pro Lys Asp Ile Asn Val Lys Trp Lys Ile Asp Gly Ser Glu Arg
145             150             155             160

Gln Asn Gly Val Leu Asn Ser Trp Thr Asp Gln Asp Ser Lys Asp Ser
            165             170             175

Thr Tyr Ser Met Ser Ser Thr Leu Thr Leu Thr Lys Asp Glu Tyr Glu
            180             185             190

Arg His Asn Ser Tyr Thr Cys Glu Ala Thr His Lys Thr Ser Thr Ser
        195             200             205

Pro Ile Val Lys Ser Phe Asn Arg Asn Glu Cys
        210             215
```

COLLAGEN TYPE X ALPHA-1 ASSAY

TECHNICAL FIELD

The present invention relates to an antibody which specifically reacts with an epitope of collagen type X alpha 1, and its use in a method of immunoassay for detecting and quantifying collagen type X alpha 1.

BACKGROUND ART

Osteoarthritis (OA) is a common joint disease which is characterized by cartilage damage and loss of joint function. The etiology of OA comprises multiple factors including aging, obesity, trauma and heredity [1]. The pathogenesis of OA is poorly understood due to the heterogeneity and complexity of this disease.

Remarkably, some characteristics of OA resemble chondrocyte differentiation processes during skeletal development by endochondral ossification. In healthy articular cartilage, chondrocytes resist proliferation and terminal differentiation. By contrast, chondrocytes in diseased cartilage progressively proliferate and develop hypertrophy. Moreover, vascularization and focal calcification of joint cartilage are initiated [2-5]. The molecular events regulating chondrocyte differentiation are still unknown, but chondrocyte hypertrophy-like changes in OA have attracted more attention for study [6-8].

Type X Collagen Alpha-1

Collagen type X alpha-1 is non-fibrillar, but forms fine pericellular filaments in association with cartilage collagen. The molecule isolated from chondrocyte cultures or from cartilage is a homotrimer of 59 kDa Collagen type X alpha-1 chains, and there have been reports of a recombinant molecule of collagen type X of approximately 75 kDa [9]. Collagen type X alpha-1 shares a similar domain structure with type VIII collagen: a central triple-helical (COL1) domain of 50 kDa is flanked by N-terminal (NC2) and C-terminal (NC1) non-triple-helical domains [10]. In addition, both collagen types represent major components of hexagonal lattice structure, in which the collagen molecules link together by interactions involving the non-triple-helical end regions.

Collagen type X alpha-1 distribution is restricted to normal fetal hypertrophic cartilage in the growth zones of long bones, vertebrae and ribs, and in adult (>21 yr) thyroid cartilage, where it may provide a scaffold to prevent local collapse as the cartilage matrix is removed during endochondral ossification [11]. It is also found in bone fracture callus, in osteoarthritic cartilage and in chondrogenic neoplasms, and may be involved in cartilage mineralization.

Osteoarthritis and Ankylosing Spondylitis

Ankylosing Spondylitis (AS) is a chronic inflammatory disease of the spine and sacroiliac joints, whereas OA is generally considered to be a non-inflammatory condition of the synovial joints, predominantly knee and hips. Chondrocyte hypertrophy and cartilage calcification are key pathological events in both joint diseases. Elevated expression of network-forming type X collagen is believed to be a specific signal for chondrocyte hypertrophy [12-15] therefore type X collagen can be used as a detectable marker for said diseases.

There are several proteins associated with hypertrophic chondrocytes, such as collagen type X, MMP13, osteopontin, osteocalcin [16], Indian Hedgehog [17], Runx2 [18], VEGF [19], HtrA1 [20] and Transglutaminase-2 (TG-2) [21]. Collagen type X and MMP13 are among the most widely used as markers of hypertrophic chondrocytes. However, synthesis of MMP13 can be induced in chondrocytes by inflammation and mechanical stress [22-23]. Therefore, collagen type X as a hypertrophic chondrocyte specific marker can indicate a phenotype alteration of chondrocytes.

Thus, a method which accurately quantifies the amount of collagen type X or its fragments in a biological sample may allow a better understanding of collagen type X pathologies or physiological processes affecting collagen type X turnover such as OA or AS. Evidently there is a need for such a method.

FIGURES

FIG. 1: Antibody specificity evaluated by two synthetic peptides: selection peptide (SFSGFLVAPM (SEQ ID NO: 1)) and truncated peptide (SFSGFLVA (SEQ ID NO: 3)).

Figure 2:
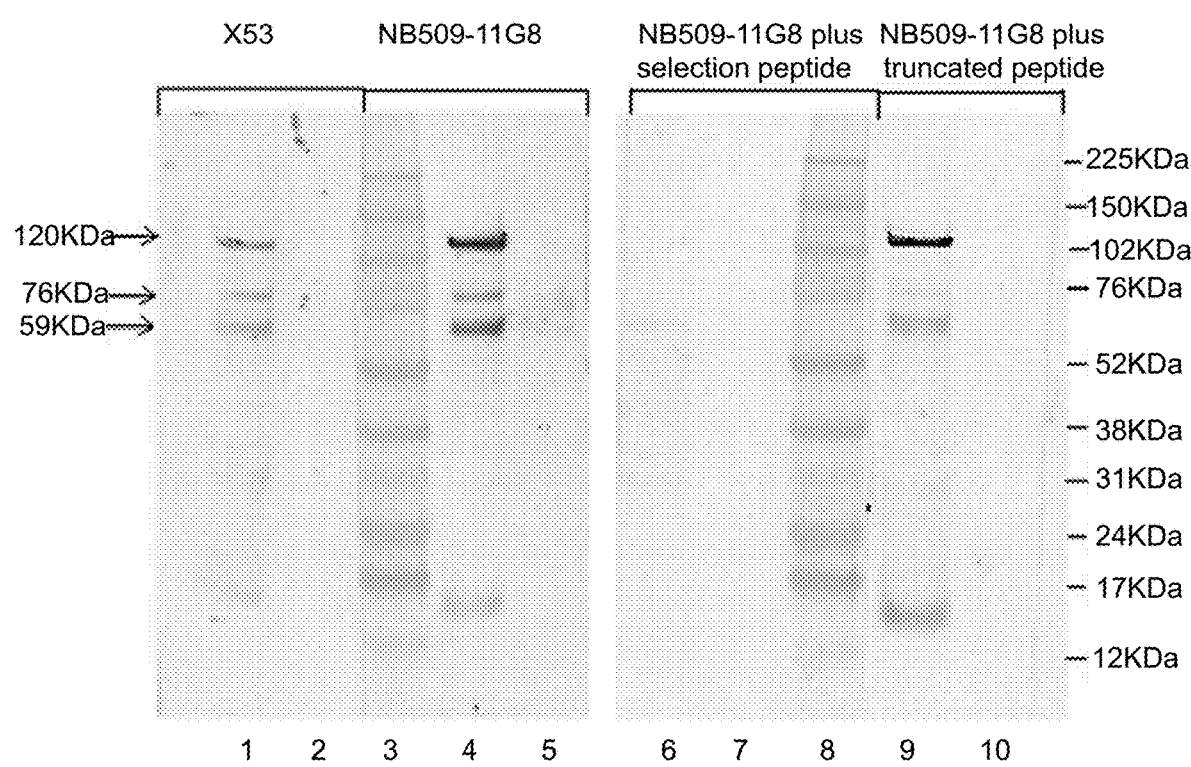

FIG. 2: Western blotting of U2-OS cell lysates. Lane 1, 4, 6 and 9: U2-OS cell lysates; Lane 2, 5, 7 and 10: RIPA buffer; Lane 3 and 8: Molecular weight standard.

DESCRIPTION OF THE INVENTION

The herein described invention relates to an antibody directed to an epitope of collagen type X alpha 1 in the NC1 domain C-terminal amino acid sequence SFSGFLVAPM-COOH (SEQ ID NO: 1) and a method of immunoassay for detecting and quantifying the amount of intact collagen type X alpha 1 and fragments thereof comprising the amino acid sequence SFSGFLVAPM-COOH (SEQ ID NO: 1).

In a first aspect, the present invention relates to an antibody, wherein said antibody specifically reacts with an epitope of collagen type X alpha 1, said epitope being comprised in the NC1 domain C-terminal amino acid sequence SFSGFLVAPM-COOH (SEQ ID NO: 1).

In a preferred embodiment of the invention, said antibody is a monoclonal antibody, or a polyclonal antibody, or an antibody fragment.

In a preferred embodiment of the invention, said antibody specifically reacts with an epitope comprised in the NC1 domain C-terminal amino acid sequence SFSGFLVAPM (SEQ ID NO: 1) of human collagen type X alpha 1.

Preferably, said antibody does not recognise or bind (or also does not recognise or bind) a truncated version of said C-terminal amino acid sequence which is . . . SFSGFLVA-COOH (SEQ ID NO: 3

It should be understood that the antibody of the present invention is an artificial product resulting from the selection of a particular antigenic sequence determined by computational means (e.g. BLAST analysis) and generated by an artificially induced immune response. It should be understood that said antibody is not a product that has been isolated from a source that occurs naturally in nature.

Preferably, said antibody is a monoclonal antibody or fragment thereof having specific binding affinity. Said monoclonal antibody or fragment thereof may preferably comprise one or more complementarity-determining regions (CDRs) selected from:

CDR-L1:
RSSQSLVHSNGYTYSN (SEQ ID NO: 6)

CDR-L2:
RVSNRFS (SEQ ID NO: 7)

```
CDR-L3:
                                   (SEQ ID. NO: 8)
SQSTHVPWT

CDR-H1:
                                   (SEQ ID NO: 9)
DTHMH

CDR-H2:
                                   (SEQ ID NO: 10)
RIDPANVNTKYDPRFQG

CDR-H3:
                                   (SEQ ID NO: 11)
SGSSP
```

Preferably the antibody or fragment thereof comprises at least 2, 3, 4, 5 or 6 of the above listed CDR sequences.

Preferably the monoclonal antibody or fragment thereof has a light chain variable region comprising the CDR sequences

```
CDR-L1:
                                   (SEQ ID NO: 6)
RSSQSLVHSNGYTYSN

CDR-L2:
                                   (SEQ ID NO: 7)
RVSNRFS

CDR-L3:
                                   (SEQ ID NO: 8)
SQSTHVPWT.
```

Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

```
                                   (SEQ ID NO: 12)
RSSQSLVHSNGYTYSNWYLQKPGQSPKLLIYRVSNRFSGVPDRF

SGSGSGTDFTLKISRVEADDLGVYFCSQSTHVPWT.
```

Preferably the monoclonal antibody or fragment thereof has a heavy chain variable region comprising the CDR sequences

```
CDR-H1:
                                   (SEQ ID NO: 9)
DTHMH

CDR-H2:
                                   (SEQ ID NO: 10)
RIDPANVNTKYDPRFQG

CDR-H3:
                                   (SEQ ID NO: 11)
SGSSP.
```

Preferably the monoclonal antibody or fragment thereof has a heavy chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

```
                                   (SEQ ID NO: 13)
DTHMHWVKQRPEQGLEWIGRIDPANVNTKYDPRFQGRATITADT

SSNTAYLQLSRLTSEDTAVYYCATSGSSPWGQGTTLTVSS.
```

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

```
                                   (SEQ ID NO: 14)
DVVMTQTPLSLPVSLGDQASISCRSSQSLVHSNGYTYSNWYLQKP

GQSPKLLIYRVSNRFSGVPDRFSGSGSGTDFTLKISRVEADDLGV

YFCSQSTHVPWTFGGGTKLEIK
``` and/or the heavy chain variable region sequence:

```
                                   (SEQ ID NO: 15)
EVQLQQSGAELVKPGASVKLSCTASGFNIKDTHMHWVKQRPEQGL

EWIGRIDPANVNTKYDPRFQGRATITADTSSNTAYLQLSRLTSED

TAVYYCATSGSSPWGQGTTLTVSS,
(CDRs bold; Framework sequences in italics)
```

In another aspect, the present invention relates to a method of immunoassay for detecting in a biological sample an epitope comprised in the NC1 domain C-terminal amino acid sequence SFSGFLVAPM-COOH (SEQ ID NO: 1) of collagen type X alpha 1, said method comprising contacting said biological sample comprising said epitope comprised in said NC1 domain C-terminal amino acid sequence SFSGFLVAPM-COOH (SEQ ID NO: 1) of collagen type X alpha 1 with an antibody of the invention, and determining the amount of binding of said antibody.

In a preferred embodiment of the invention, said method of immunoassay is used to quantify the amount of intact collagen type X alpha 1 and fragments thereof comprising the amino acid sequence SFSGFLVAPM (SEQ ID NO: 1) in biofluid, wherein said biofluid may be, but is not limited to, synovial fluid, serum or plasma.

In a preferred embodiment of the invention, said method of immunoassay may be, but is not limited to, a competition assay or a sandwich assay.

In a preferred embodiment of the invention, said method of immunoassay may be, but is not limited to, a radioimmunoassay or an enzyme-linked immunosorbent assay.

It should be understood that intact collagen type X alpha 1 and fragments thereof comprising the amino acid sequence SFSGFLVAPM (SEQ ID NO: 1) can be detected and quantified using assay methods other than that of the present invention. Such methods include quantitative chromatographic techniques, 1D- and 2D-electrophoresis techniques, and quantitative mass spectrometry.

In a preferred embodiment of the invention, said method of immunoassay further comprises correlating the quantity of intact collagen type X alpha 1 and fragments thereof comprising said amino acid sequence SFSGFLVAPM (SEQ ID NO: 1) determined by said method with standard disease samples of known disease severity to evaluate the severity of a disease associated with collagen type X alpha 1.

In a preferred embodiment of the invention, said method of immunoassay further comprises correlating the quantity of intact collagen type X alpha 1 and fragments thereof comprising said amino acid sequence SFSGFLVAPM (SEQ ID NO: 1) determined by said method with standard Osteoarthritis samples of known severity.

In a preferred embodiment of the invention, said method of immunoassay further comprises correlating the quantity of intact collagen type X alpha 1 and fragments thereof comprising said amino acid sequence SFSGFLVAPM (SEQ ID NO: 1) determined by said method with standard Ankylosing Spondylitis samples of known severity.

Preferably, the present invention relates to a method for evaluating the severity of a disease associated with collagen type X alpha 1 in a human patient, such as Osteoarthritis or Ankylosing Spondylitis, said method comprising:
  obtaining a biological sample from a patient;
  contacting said biological sample with an antibody of the invention;
  determining the amount of binding of said antibody using either a radioimmunoassay or an enzyme-linked immunosorbent assay, thereby quantifying the amount of intact collagen type X alpha 1 and fragments thereof comprising the amino acid sequence SFSGFLVAPM (SEQ ID NO: 1) in said biological sample;
  correlating the quantity of intact collagen type X alpha 1 and fragments thereof comprising said amino acid sequence SFSGFLVAPM (SEQ ID NO: 1) with standard samples of a disease associated with collagen type X alpha 1, such as Osteoarthritis or Ankylosing Spondylitis; and
  determining the severity of the disease associated with collagen type X alpha 1, such as Osteoarthritis or Ankylosing Spondylitis, in said patient.

In another aspect, the present invention relates to an assay kit for determining the quantity of intact collagen type X alpha 1 and fragments thereof comprising the amino acid sequence SFSGFLVAPM (SEQ ID NO: 1) in a biological sample, said kit comprising an antibody as described herein and at least one of:
  a streptavidin coated 96 well plate
  a biotinylated peptide Biotin-L-SFSGFLVAPM-COOH (SEQ ID NO: 2), wherein L is an optional linker
  a secondary antibody for use in a sandwich immunoassay
  a calibrator peptide comprising the sequence SFSGFLVAPM (SEQ ID NO: 1)
  an antibody biotinylation kit
  an antibody HRP labeling kit
  an antibody radiolabeling kit
  an assay visualization kit Definitions "Antibody" as used herein refers to a monoclonal antibody, a polyclonal antibody, or an antibody fragment, such as Fab, F(ab')$_2$, Fv, or scFv fragments etc., or a chemically modified derivative of any of these.

"C-Col10" is used to distinguish the herein described collagen type X assay from the collagen type X assays known in the art which are not based on the specific binding of epitopes comprised within the amino acid sequence SFSGFLVAPM (SEQ ID NO: 1).

EXAMPLES

Materials and General Considerations

All reagents used in the experiments were high-standard chemicals from companies such as VWR (Rødovre, Denmark) and Sigma Aldrich (Brøndby, Denmark). The synthetic peptides used for monoclonal antibody production and validation were 1) Immunogenic peptide: KLH-CGG-SFSGFLVAPM-COOH (KLH=Keyhole Limpet Hemocyanin) (SEQ ID NO: 4) 2) Screening peptide: Biotin-SFSGFLVAPM-COOH (SEQ ID NO: 2), and 3) Selection peptide: SFSGFLVAPM-COOH (SEQ ID NO: 1). All synthetic peptides were purchased from Thermo Fisher, Beijing, China.

Example 1. Monoclonal Antibody Generation—NB509-11G8

The sequence for the C-terminal NC1 domain type X collagen was selected from homology between species and uniqueness among other ECM proteins by protein blasting. It was directed against the C-terminal NC1 domain and selected for minimization of homology to other human proteins and optimization of immunogenicity. The resulting epitope amino acid sequence was SFSGFLVAPM-COOH (SEQ ID NO: 1). Generation of monoclonal antibodies was initiated by subcutaneous immunization of 6 week old Balb/C mice with 200 µl emulsified antigen (Freund's adjuvant) and 60 µg of the collagen type X alpha 1 epitope sequence (KLH-CGG-SFSGFLVAPM-COOH (SEQ ID NO: 4)). Two further immunizations of 30 µg immunogen in 200 µl emulsified antigen were given 2 weeks apart and four final immunizations of 30 µg immunogen in 200 µl emulsified antigen were given 3 weeks apart. Blood samples were collected from the 3rd immunization. Each sample was stored at −20° C. prior to analysis.

At each blood sampling, the serum titer was determined and the mouse with highest antiserum titer was selected for fusion. After the final immunization, this mouse was rested for 1 month and then boosted intravenously with 50 µg immunogen in 100 µl 0.9% sodium chloride solution three days before isolation of the spleen for cell fusion. The fusion procedure was performed as described by Gefter et al [24]. Briefly, mouse spleen cells were fused with SP2/0 myeloma fusion partner cells. The hybridoma cells were cloned using a semi-solid medium method and transferred into 96-well microtiter plates for further growth and incubated in a CO2-incubater. Standard limited dilution was used to promote monoclonal growth. The supernatants were screened for reactivity and selectivity against the calibrator peptide (SFSGFLVAPM (SEQ ID NO: 1)), deselection peptide (DMDYLPRVPNQ (SEQ ID NO: 5)) and truncated peptide (SFSGFLVA (SEQ ID NO: 3)). Biotin-SFSGFLVAPM-COOH (SEQ ID NO: 2) was used as screening peptide. The isotype of the monoclonal antibodies was determined using the Clonotyping System-HRP kit, cat. 5300-05 (Southern Biotech, Birmingham, Ala., USA).

Clone Characterisation

Human osteosarcoma cell lines (U2-OS; collagen X producing cell line) were purchased from ATCC (USA) and cultivated in DMEM medium containing 10% FBS, 2 mM L-Glutamine, 100 units/ml penicillin and 100 ug/ml streptomycin. Cells were grown in T25 flasks in a 37° C. incubator at 5% CO2, changing the medium every two or three days. When the cells reached 90% confluency the cell lysates were prepared using RIPA lysis buffer with following procedure: the cell media was removed and the cells washed twice with PBS, followed by adding cold RIPA lysis buffer (25 mM Tris-HCl pH7, 6; 150 mM NaCl, 1% Sodium deoxycholate acid). An EDTA free cocktail tablet was added to the flask then RIPA buffer was distributed to cover the whole surface of flask and incubated on ice for 10 minutes. The cells were scraped and centrifuged at 10,000 RPM at 4° C. for 10 minutes and the supernatants stored at −20° C. until use.

U2-OS lysates were electrophoresed on 4-12% Bis-Tris gradient gel under reducing conditions using MES SDS running buffer. Protein bands were blotted onto a nitrocellulose membrane using the Invitrogen i-Blot gel transfer system according to manufacturer's instruction. The membrane was blocked in blocking buffer (5% skimmed milk in Tris-buffered saline with Tween (TBST)) overnight at 4° C. The monoclonal antibody, NB509-11G8 and commercial collagen type X antibody X53 (for comparison purposes) were applied in a concentration of 1 µg/ml in TBST with 5% skim milk powder and shaken overnight at 4° C. After washing 6 times with TBST, the anti-mouse secondary antibody was applied in 1:5000 in TBST with shaking at RT for 2 hours. The membrane was washed 6 times with TBST and the bands were visualized using an electro-chemiluminesence machine. To confirm the specificity of bands, a blocking western blot was performed with the same procedure, however with the addition of 3 µg/ml selection peptide (SFSGFLVAPM (SEQ ID NO: 1)) or truncated peptide (SFSGFLVA (SEQ ID NO: 3)) into the NB509-11G8 solution.

Clone Selection and Characterization

The subtype was determined to be an IgG1,k subtype. Antibody NB509-11G8 was found to be reactive with the selection peptide (SFSGFLVAPM (SEQ ID NO: 1)) whilst being non-reactive with the deselection peptide (DMDYLPRVPNQ (SEQ ID NO: 5)) and the truncated peptide (SFSGFLVA (SEQ ID NO: 3)) (no inhibition observed in the preliminary assays) (FIG. 1 shows the difference in reactivity of the antibody with the selection peptide and the truncated peptide). From the Western Blot analysis (FIG. 2) it was seen that the commercial antibody X53 and the collagen type X alpha 1 NC1 domain C-terminal epitope specific monoclonal antibody NB509-11G8 recognized three bands with molecular sizes around 59 kDa, 76 kDa and 120 kDa. The bands at 59 and 120 kDa are the collagen type X monomer and dimer, respectively, and the band at 76 kDa is assumedly the previously reported recombinant collagen type X molecule [9]. All three bands could be inhibited by the selection peptide blocking experiment, whereas no inhibition was observed whilst using the truncated peptide. A further Western blot analysis of collagen type X alpha 1 treated with collagenase demonstrated binding of NB509-11G8 to multiple fragments, confirming that NB509-11G8 binds fragments of collagen type X alpha 1 as well as the intact molecule.

The antibody NB509-11G8 generated was sequenced and the CDRs determined. The sequence of the chains are as follows (CDRs in bold; Framework sequence in Italics; Constant region underlined):

```
Heavy chain: Amino acid sequence (438 aa)
(Mouse IgG1 isotype)
                                          (SEQ ID NO: 16)
EVQLQQSGAELVKPGASVKLSCTASGFNIKDTHMHWVKQRPEQGL

EWIGRIDPANVNTKYDPRFQGRATITADTSSNTAYLQLSRLTSED

TAVYYCATSGSSPWGQGTTLTVSSAKTTPPSVYPLAPGSAAQTNS

MVTLGCLVKGYFPEPVTVTWNSGSLSSGVHTFPAVLQSDLYTLSS

SVTVPSSTWPSETVTCNVAHPASSTKVDKKIVPRDCGCKPCICTV

PEVSSVFIFPPKPKDVLTITLTPKVTCVVVDISKDDPEVQFSWFV

DDVEVHTAQTQPREEQFNSTFRSVSELPIMHQDWLNGKEFKCRVN

SAAFPAPIEKTISKTKGRPKAPQVYTIPPPKEQMAKDKVSLTCMI

TDFFPEDITVEWQWNGQPAENYKNTQPIMDTDGSYFVYSKLNVQK

SNWEAGNTFTCSVLHEGLHNHHTEKSLSHSPGK

CDR-H1:
                                           (SEQ ID NO: 9)
DTHMH

CDR-H2:
                                          (SEQ ID NO: 10)
RIDPANVNTKYDPRFQG

CDR-H3:
                                          (SEQ ID NO: 11)
SGSSP

Light chain: Amino acid sequence (238 aa)
(mouse Kappa isotype)
                                          (SEQ ID NO: 17)
DVVMTQTPLSLPVSLGDQASISCRSSQSLVHSNGYTYSNWYLQKP

GQSPKLLIYRVSNRFSGVPDRFSGSGSGTDFTLKISRVEADDLGV

YFCSQSTHVPWTFGGGTKLEIKRADAAPTVSIFPPSSEQLTSGGA

SVVCFLNNFYPKDINVKWKIDGSERQNGVLNSWTDQDSKDSTYSM

SSTLTLTKDEYERHNSYTCEATHKTSTSPIVKSFNRNEC

CDR-L1:
                                          (SEQ ID. NO: 6)
RSSQSLVHSNGYTYSN

CDR-L2:
                                          (SEQ ID. NO: 7)
RVSNRFS

CDR-L3:
                                          (SEQ ID. NO: 8)
SQSTHVPWT_
```

Example 2. Enzyme-Linked Immunosorbent Assay (ELISA)

ELISA Assay Generation/Optimization

The buffer type, coater concentration, antibody concentration and incubation conditions were optimised using standard methods.

C-Col10 ELISA Protocol

The competitive C-Col10 ELISA procedure was as follows: A 96-well streptavidin-coated ELISA plate from Roche, cat. 11940279, was coated with the biotinylated peptide Biotin-SFSGFLVAPM-COOH (SEQ ID NO: 2) dissolved in coater buffer (25 mM PBS-BTB, pH 7.4) at 4 ng/ml in 100 µl, incubated for 30 min at 20° C. in the dark and subsequently washed in washing buffer (20 mM Tris, 50 mM NaCl, pH 7.2). Thereafter 20 µl of peptide calibrator or sample was added to the appropriate wells, followed by 100 µl of HRP-conjugated monoclonal antibody NB509-11G8 (labeled with HRP using Lightning-Link™ HRP Conjugation Kit (Innova Biosciences, Babraham, Cambridge, UK), according to the manufacturer's instructions) dissolved in incubation buffer (25 mM PBS-BTB, pH 7.4) at 190 ng/ml. The plate was incubated for 20 hours at 4° C. and washed. Finally, 100 µl tetramethylbenzinidine (TMB) (Kem-En-Tec cat.: 438OH) was added, the plate was incubated for 15 min at 20° C. in the dark and the reaction was stopped by addition of 100 µl of stopping solution (2M $H_2SO_4$). The plate was analyzed in an ELISA reader at 450 nm with 650 nm as the reference (Molecular Devices, SpectraMax M, CA, USA).

Technical Evaluation of C-Col10 ELISA

The lower detection limit (LDL) was calculated from 21 determinations of the lowest standard (the zero standard) and calculated as the mean +3× standard deviation. The LDL for the assay was 0.062 ng/mL. The inter- and intra-assay variation was determined by 10 independent runs of 8 QC samples, with each run consisting of two replicas of double determinations of the samples.

The inter- and intra-assay variation was a mean 13.18% and 4.19% respectively. For each assay a master calibrator prepared from synthetic peptides accurately quantified by amino acid analysis was used for calibration purposes.

The linearity-dilution of human serum is acceptable down to 1:4 and the measurement range is 2-0.088 ng/mL.

Example 3. Correlation Between C-Col10 and C2M

Matrix metalloprotein derived collagen type II fragment (C2M) has been shown to be a marker of cartilage degradation [25]. The C-Col10 assay significantly correlated with cartilage degradation marker measured by C2M assay (Pearson r=0.5748, P<0.0001). This suggests that hypertrophy-like changes in OA may be associated with cartilage degradation. Therefore, measurement of collagen type X as a marker of hypertrophic chondrocytes may offer an alternative method for monitoring cartilage degradation in OA.

Example 4. Immunolocalisation

A further use for antibody NB509-11G8 can be found in immunolocalisation studies. 5 human cartilage samples were processed using the following procedure: fixed and decalcified cartilage were embedded in paraffin wax and cut into 5 µm thick sections. Sections were melted at 60° C., deparaffinized, and hydrated. For collagen type X, antigen retrieval was performed using Pronase E (Roche) at 37° C. for 15 minutes, while sections were demarked in the citrate buffer pH 6.0 at 60° C. overnight. Unspecific binding was blocked with 0.5% casein in TBS buffer at RT for 20 minutes. Then NB509-11G8 solution or normal mouse IgG solution (negative control) were incubated with sections at 4° C. overnight (20±1 h). Immunoactivity was detected by using peroxidase labeled anti-mouse system and diaminobenzidine (DAB, Dako, Denmark) as the chromogen. Sections were counter stained with Mayer's acidic hematoxylin for 12 seconds.

The distribution of collagen type X was tested using standard immunohistochemistry methods known in the art. Collagen type X was predominately detected in the deep zone and calcified cartilage in a mild OA sample, of which the surface was uneven and showed surface fibrillation. When vertical fissures extended into the mid zone, a strong signal of collagen type X was observed in the mid zone. However, when surface erosion, cartilage lesions and clustering of chondrocytes were present, collagen type X stained the matrix around clustered chondrocytes.

Example 5. Study of C-Col10 in OA Patients

Serum Samples

Serum samples were retrieved from a C4Pain study (n=271 with Kellgren-Lawrence score ranging from 0-4; briefly, the K-L score is a scoring system based on x-ray radiographs of a patient's joints, wherein the score is determined by a trained radiographer, and consists of measuring joint space narrowing, osteophytes and sclerosis). In this study, the OA population was recruited based on intensity of knee joint pain, with the patients being selected across the pain score range of from 0 to 100 on a Western Ontario and McMaster Universities Osteoarthritis Index (WOMAC) pain scale. Two plain X-ray examinations in standing position were performed. The Kellgren-Lawrence score ranging from 0-4 of participants were obtained. Serum was collected upon overnight fasting prior to surgery or during consultation. The study was approved by The Ethical Committee of Northern Jutland (VEK no.: N-20100094). They were conducted according to the Principal of Good Clinical Practice and according to the Declaration of Helsinki. All patients provided written informed consent.

Assessment of C-Col10 in OA Serum Samples 271 subjects were stratified into 5 groups based on their KL score (Table 1). There was significant difference in the Col10 levels of KL0 and KL2 (p=0.04). The mean value of Col10 in KL3 and KL 4 groups were 1.5 and 1.7 times the mean value of Col10 in KL0 group, respectively, however, this was not significant (due to insufficient number of study participants).

The results demonstrate a general increase in Col10 compared to KL score, which shows the usefulness of using the herein described Col10 immunoassay for OA diagnostic purposes.

TABLE 1

Serum levels of Col10 in 271 samples divided by KL score. The data is shown as mean [95%-CI]. Col10: C-terminus of Col10 assay; KL score: Kellengren-Lawrence score. Unpaired t-test was applied to compare to log transformed data when compare the levels.

| KL score | Number of Female/Male | Age | BMI | C-Col10 pg/ml | P value |
|---|---|---|---|---|---|
| 0 | 4/6 | 62.5 (57.3-67.7) | 25.4 (23.7-27.0) | 52 (24-80) | — |
| 1 | 31/28 | 63.7 (61.6-65.8) | 27.0 (26.0-28.1) | 65 (54-76) | 0.11 |
| 2 | 79/65 | 64.7 (63.5-65.9) | 28.2 (27.5-28.8) | 86 (73-98) | 0.04* |
| 3 | 17/19 | 64.3 (61.9-66.7) | 29.3 (27.4-31.2) | 80 (60-101) | 0.07 |
| 4 | 12/10 | 67.8 (64.4-71.2) | 29.5 (27.8-31.2) | 87 (47-128) | 0.28 | p value calculated with respect to KL = 0.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

1. Abhishek, A. and M. Doherty, Pathophysiology of articular chondrocalcinosis role of ANKH. Nat Rev Rheumatol, 2011; 7:96-104.
2. Kronenberg, H. M., Developmental regulation of the growth plate. Nature, 2003; 423:332-6.
3. Pfander, D., B. Swoboda, and T. Kirsch, Expression of early and late differentiation markers (proliferating cell nuclear antigen, syndecan-3, annexin VI, and alkaline phosphatase) by human osteoarthritic chondrocytes. Am J Pathol, 2001; 159:1777-83.
4. von der Mark, K., et al., Type X collagen synthesis in human osteoarthritic cartilage. Indication of chondrocyte hypertrophy. Arthritis Rheum, 1992; 35:806-11.
5. Fuerst, M., et al., Calcification of articular cartilage in human osteoarthritis. Arthritis Rheum, 2009; 60:2694-703.
6. Dreier, R., Hypertrophic differentiation of chondrocytes in osteoarthritis: the developmental aspect of degenerative joint disorders. Arthritis Res Ther, 2010; 12:216.
7. Pitsillides, A. A. and F. Beier, Cartilage biology in osteoarthritis—lessons from developmental biology. Nat Rev Rheumatol, 2011; 7:654-63.
8. van der Kraan, P. M. and W. B. van den Berg, Chondrocyte hypertrophy and osteoarthritis: role in initiation and progression of cartilage degeneration? Osteoarthritis Cartilage, 2012; 20:223-32.
9. Frischholz, S., et al., J. Biol. Chem., 1998; 273:4547.
10. Yamaguchi, N., et al. J. Biol. Chem., 1989; 264:16022.
11. Olsen, B. J., and Ninomiya, Y., in: Guidebook to the Extracellular Matrix and Adhesion Proteins, Kreis, T., and Vale, R. (eds.), Oxford University Press, Oxford, pp. 32-48 (1993).
12. Schmid, T. M., and Linsenmayer, T. F., in: Structure and Function of Collagen Types, Mayne, R., and Burgeson, R. E. (eds.), Academic Press Inc., pp. 223-259 (1987).
13. Rucklidge, G. J., et al., Matrix Biol., 1996; 15:73.
14. Aigner, T., et al., Histochem. Cell Biol., 1997; 107:435.
15. Girkontaite, I., et al., Matrix Biol., 1996; 15:231.
16. Gerstenfeld, L. C. and F. D. Shapiro, Expression of bone-specific genes by hypertrophic chondrocytes: implication of the complex functions of the hypertrophic chondrocyte during endochondral bone development. J Cell Biochem, 1996; 62:1-9.
17. Wei, F., et al., Activation of Indian hedgehog promotes chondrocyte hypertrophy and upregulation of MMP-13 in human osteoarthritic cartilage. Osteoarthritis Cartilage, 2012; 20:755-63.
18. Dong, Y. F., et al., Wnt induction of chondrocyte hypertrophy through the Runx2 transcription factor. J Cell Physiol, 2006; 208:77-86.
19. Horner, A., et al., Immunolocalisation of vascular endothelial growth factor (VEGF) in human neonatal growth plate cartilage. J Anat, 1999; 194:519-24.
20. Tsuchiya, A., et al., Expression of mouse HtrA1 serine protease in normal bone and cartilage and its upregulation in joint cartilage damaged by experimental arthritis. Bone, 2005; 37:323-36.
21. Huebner, J. L., et al., Transglutaminase 2 is a marker of chondrocyte hypertrophy and osteoarthritis severity in the Hartley guinea pig model of knee OA. Osteoarthritis Cartilage, 2009; 17:1056-64.
22. Fitzgerald, J. B., et al., Shear- and compression-induced chondrocyte transcription requires MAPK activation in cartilage explants. J Biol Chem, 2008; 283:6735-43.
23. Goldring, M. B., et al., Defining the roles of inflammatory and anabolic cytokines in cartilage metabolism. Ann Rheum Dis, 2008; 67:75-82.
24. Gefter M L, Margulies D H, Scharff M D. A simple method for polyethylene glycol-promoted hybridization of mouse myeloma cells. Somatic Cell Genet., 1977; 3:231-6.
25. Bay-Jensen, A. C., et al., Enzyme-linked immunosorbent assay (ELISAs) for metalloproteinase derived type II collagen neoepitope, CIIM—increased serum CIIM in subjects with severe radiographic osteoarthritis. Clin Biochem, 2011; 44:423-9.

What is claimed is:

1. A monoclonal antibody that comprises a light chain comprising complementarity-determining regions (CDRs) with amino acid sequences of SEQ ID NOS: 6-8 and a heavy chain comprising CDRs with amino acid sequences of SEQ ID NOS: 9-11, wherein said monoclonal antibody specifically binds to an NC1 domain C-terminal amino acid sequence SFSGFLVAPM-COOH (SEQ ID NO: 1) of human collagen type X alpha 1.

2. A method of immunoassay for detecting in a biofluid sample an epitope in the NC1 domain of collagen type X alpha 1 with the C-terminal amino acid sequence SFSGFLVAPM-COOH (SEQ ID NO: 1), said method comprising:
  obtaining a biofluid sample from a patient,
  contacting said biofluid sample with the monoclonal antibody as claimed in claim 1, and
  detecting an amount of binding of said monoclonal antibody to the epitope in the NC1 domain of collagen type X alpha 1 with the C-terminal amino acid sequence SFSGFLVAPM-COOH (SEQ ID NO: 1).

3. The method of immunoassay as claimed in claim 2, wherein said method is used to quantify the amount of intact collagen type X alpha 1 and fragments thereof comprising the amino acid sequence SFSGFLVAPM (SEQ ID NO: 1) in biofluid.

4. The method of immunoassay as claimed in claim 2, wherein said method is a competition assay or a sandwich assay.

5. The method of immunoassay as claimed in claim 2, wherein said method is a radioimmunoassay or an enzyme-linked immunosorbent assay.

6. The method of immunoassay as claimed in claim 3, wherein the quantity of intact collagen type X alpha 1 and fragments thereof comprising said amino acid sequence SFSGFLVAPM (SEQ ID NO: 1) determined by said method is used to evaluate severity of a disease associated with collagen type X alpha I as compared with standard disease samples of known disease severity.

7. The method of immunoassay as claimed in claim 6, wherein the disease associated with collagen type X alpha I is osteoarthritis.

8. The method of immunoassay as claimed in claim 6, wherein the disease associated with collagen type X alpha I is ankylosing spondylitis.

* * * * *